United States Patent [19]

Cherukuri et al.

[11] Patent Number: 4,803,082
[45] Date of Patent: Feb. 7, 1989

[54] FLAVOR AND SWEETNESS ENHANCEMENT DELIVERY SYSTEMS AND METHOD OF PREPARATION

[75] Inventors: Subraman R. Cherukuri, Towaco; Steven M. Faust, Stanhope, both of N.J.; Daniel A. Orlandi, Flushing, N.Y.

[73] Assignee: Warner-Lambert Company, Morris Plains, N.J.

[21] Appl. No.: 114,483

[22] Filed: Oct. 28, 1987

[51] Int. Cl.$^4$ ............................ A61K 9/68; A23G 3/30
[52] U.S. Cl. ...................................... 424/493; 426/3; 426/5; 424/489; 424/48
[58] Field of Search ................. 426/3, 5; 424/48, 493, 424/489

[56] References Cited

U.S. PATENT DOCUMENTS

| | | | |
|---|---|---|---|
| 3,857,962 | 12/1974 | Westall et al. | 426/3 |
| 4,208,431 | 6/1980 | Friello et al. | 426/3 |
| 4,217,368 | 8/1980 | Witzel et al. | 426/5 |
| 4,228,198 | 10/1980 | Burge et al. | 426/656 |
| 4,238,475 | 12/1980 | Witzel et al. | 426/3 |
| 4,292,336 | 9/1981 | Latymer | 426/548 |
| 4,412,984 | 11/1983 | van der Loo et al. | 426/3 |
| 4,590,075 | 5/1986 | Wei et al. | 426/5 |
| 4,597,970 | 7/1986 | Sharma et al. | 426/5 |
| 4,642,235 | 2/1987 | Reed et al. | 426/5 |

Primary Examiner—Ellis P. Robinson
Assistant Examiner—P. J. Ryan
Attorney, Agent, or Firm—Daniel Scola; Henry Jeanette; Gary M. Nath

[57] ABSTRACT

A free-flowing particulate delivery system for providing enhanced flavor and sweetness to comestible compositions comprising a powdered flavor composition encapsulated in a matrix comprising thaumatin, monellin, dihydrochalcones and mixtures thereof, and a hydrophobic wax or fat. The delivery system is particularly useful in chewing gums, confectioneries and pharmaceutical preparations as well as other food products.

23 Claims, 1 Drawing Sheet

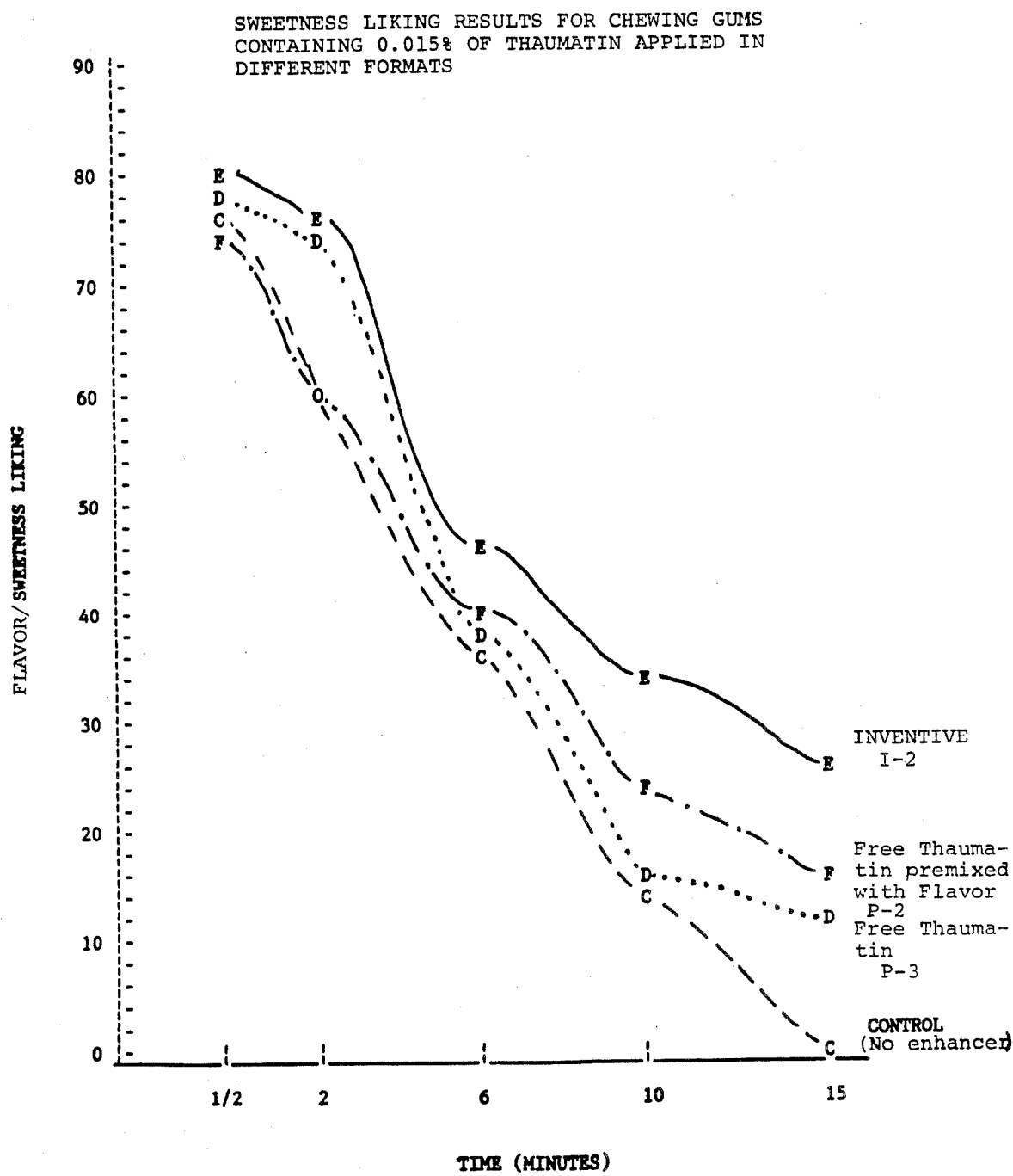

FLAVOR AND SWEETNESS ENHANCEMENT DELIVERY SYSTEMS AND METHOD OF PREPARATION

FIELD OF THE INVENTION

This invention relates to a novel flavor delivery system for use in comestibles such as chewing gum compositions, confectioneries, pharmaceuticals and food and beverage products. More particularly, this invention relates to a delivery system which provides enhancement of flavor and sweeteners with a controlled sustained release and intensity. The delivery systems use a flavor enhance with the encapsulating matrix which surround the flavor particles.

BACKGROUND OF THE INVENTION

Sweetener delivery systems are well known in the art. Most recently, U.S. Pat. No. 4,597,970 to Sharma et al. discloses chewing gum compositions capable of effected a controlled release of the sweetener. This reference teaches a high intensity sweetener core encapsulated within a hydrophobic matrix consisting essentially of lecithin, a fatty acid or wax having a melting point in the range of 25° C. to about 100° C. and a glyceride. This matrix requires the use of lecithin as a surface wetting agent for difficult to coat sweeteners such as aspartame. Flavoring agents are disclosed as being incorporated in the core along with the sweetener. The extension of sweetener is due entirely to the delayed release caused by the encapsulating coating.

Numerous chewing gum patents have disclosed the use of thaumatin (talin) and monellin as flavor enhancers and sweeteners. For example, U.S. Pat. No. 4,412,984 discloses the use of thaumatin or monellin in oral compositions at levels sufficient to enhance flavor but below the detectable sweetness threshold of these materials. Column 2 of this reference discloses chewing gum compositions containing polyvinylacetate, calcium carbonate and thaumatin, the later being disclosed as having a sweetness threshold of about 0.05% and at flavor potentiation levels of 0.01 to 0.03%. The thaumatin or monellin is directed added to the oral composition without being adsorbed or encapsulated.

U.S. Pat. No. 4,642,235 discloses a center-filled chewing gum having the center-fill comprised of thaumatin or monellin, in amounts of 5 to 100 ppm by weight, as the sweetener. The thaumatin or monellin is directly mixed with the carbohydrate syrup and flavors and incorporated into the gum shell.

U.S. Pat. No. 4,292,336 discloses a heat-stable sweetening composition containing a peptide, sweetener such as thaumatin, being mixed with gelatin in a weight ratio of gelatin to sweetener of 1:1 to 100:1. Incorporation of this composition into powders, tablets, dragees, semisolids and liquids is disclosed.

U.S. Pat. No. 4,096,285 discloses a sweetener composition containing a protein sweetener such as thaumatin, monellin or saccharin together with a sweetener modified selected from the group consisting of aldohexuronic acids and salts, amides and lactones thereof. The modifier is present in amounts sufficient to reduce the sweet aftertaste of the sweeteners and the bitter aftertaste of the saccharin.

Other patents which discuss thaumatin and monellin relate to their extraction from their source plants and purification for human consumption. Examples are U.S. Pat. Nos. 4,122,205 and 4,228,198.

Additionally, surface coating of chewing gum compositions with a rolling compound comprising from 0.5 to 100 ppm of monellin and thaumatin are taught in U.S. Pat. No. 4,562,076.

The prior art has focused on using thaumatin and monellin either directly into various comestible products or mixing them with gelatin or other powdered compounds to modify its sweeteners. It is apparent that a need exists for an encapsulating particulate delivery system such as the inventive one, which comprises powdered flavor composition contained in a hydrophobic matrix of fat or wax and a flavor/sweetener enhancer. The invention delivery systems are intended for use in food products, beverages, pharmaceuticals, confectionaries, chewing gum products, mouthwashes, toothpastes and other oral products intended for oral hygiene or ingestion.

SUMMARY OF THE INVENTION

The inventive delivery system contemplates a delivery system for virtually any powdered flavor compositions and combinations of these. In particular, it is especially directed to those flavors which are spray dried. The term "spray dried flavor" is meant to include the powdered product resulting from a natural or synthetic flavoring agent, e.g. an oil or essence, being adsorbed into a particulate carrier medium such as a starch, gum arabic, sugar, maltodextrin, corn syrup, polyol and the like. These spray dried materials may be formed by any conventional spray drying techniques as well as through extrusion, grinding or coacervation methods.

The delivery systems are intended to be incorporated into comestibles for the purpose of enhancing the perception of sweetness and flavor. Thus, while the addition of monellin, thaumatin and dihydochalcones and the like are incorporated for purposes known in the art, the delivery system composition as a whole is unique. By means of incorporating these flavor and sweetness enhancers into the hydrophobic encapsulating matrix, the powdered flavor is in intimate contact with the enhancers for maximum enhancement effect.

The delivery system in its final form is a particulate, free flowing material, intended to provide enhanced flavor and sweetness to comestible compositions, said delivery system comprising:
(a) a powdered flavor composition; and
(b) an encapsulating matrix for said powdered flavor composition;
wherein said matrix comprises a flavor and sweetener enhancer and a hydrophobic material selected from the group consisting of fats, waxes and mixtures thereof.

BRIEF DESCRIPTION OF THE DRAWING

FIG. I—graph showing panels evaluation results (blind studies) for four different chewing gum compositions.

DETAILED DESCRIPTION AND PREFERRED EMBODIMENTS

As previous discussed, the powdered flavor compositions may be selected from any available flavor which is capable of being spray dried or incorporated into or onto a solid carrier composition. Sugar and polyols are the most common solid carriers used for spray drying flavors, although a variety of other conventional materials are available. The particular powdered flavor composition is not critical to the invention in any manner. Generally, a spray dried flavor composition will have carrier present in amounts of about 50 to 95% by weight, with the remainder comprising flavor oils or essences. The core of the delivery system is the powdered flavor composition. In addition to the flavor composition, any member of additional ingredients may be added such as sweeteners, drugs, fiber, etc.

Surrounding the core is an encapsulating, hydrophobic matrix containing the flavor and sweetener enhancer. The hydrophobic matrix comprises a fat or wax in combination with a flavor and sweetener enhancer. The fats may be selected from any number of conventional materials such as fatty acids, glycerides, polyglycerol esters, sorbitol esters, and mixtures thereof. Examples of fatty acids include hydrogenated or partially hydrogenated vegetable oils such as palm oil, palm kernel oil, peanut oil, rapeseed oil, rice bran oil, soybean oil, cottonseed oil, sunflower oil, safflower oil and mixtures thereof. Other fatty acid oils are contemplated. Glycerides which are useful include mono-, di- and tri-glycerides.

Waxes useful are chosen from among the group consisting of natural or synthetic waxes and mixtures thereof. Nonlimiting examples include paraffin wax, petrolatum, carbowax, microcrystalline wax, beeswax, carnuba wax, candellila wax, lanolin, bayberry wax, sugar cane, spermaceti wax, rice bran wax and combinations thereof.

The fats and waxes may be used individually or in combination in amounts varying from about 10 to about 70% by weight of the delivery system, and preferably in amounts of about 40 to about 58% by weight. When used as a combination, the fat and wax are preferably present in a ratio of about 70:10 to about 85:15 of fat to wax. The hydrophobic matrix should have a melting point below about 100° C. to ensure it will not require temperatures above those which will denature or degrade the flavor/sweetener enhancers during preparation.

The flavor/sweetener enhancers may be chosen from numerous well known enhancer ingredients but of particular importance in the instant invention are thaumatin, monellin and hydrochalcones. Mixtures of these are useful. The flavor/sweetener enhancers are intended to be used at levels which are sufficient to impart an enhanced effect to the flavor or sweetness present in the comestible product into which they are added. They may be present in amounts of from 1 to about 30% by weight of the delivery system, but preferably in amounts of about 5 to about 20% and most preferably in amounts of about 5 to about 10% by weight.

It is well known that soluble proteins such as thaumatin and monellin are stable at certain temperatures below 100° C. and at a pH of about 5.5. The literature has disclosed thaumatin to be about 2,000 to 3,000 times the sweetness of sugar, with a solubility of about 60 g/100 ml water. It is known also that the use of these proteins as sweeteners results in a slight delay of sweetness perception, presumably due to the gradual build-up of the sweetener concentration to the perceptible thresholds level. These properties render these materials very susceptible to variations in pH, heat, water and chemical exposure when incorporated into products such as comestibles and particularly in chewing gum compositions. This concern is of little moment in the inventive delivery systems, however, due to the protective nature of the hydrophobic matrix.

The process of preparing the delivery systems in one embodiment comprises providing a homogeneous, hydrophobic molten mixture comprising a fat or wax at a temperature below the denaturizing or degrading level of the sweetener/flavor enhancer (e.g., below about 100° C.); admixing the sweetener/flavor enhancer to obtain homogeniety, while maintaining the temperature below about 100° C. and more specifically at about 85° to about 95° C.; spraying the thus formed hydrophobic/flavor enhancer into a stream of suspended flavor particles such that hydrophobic mixture coats the flavor particles and simultaneously congeals to form a dry, particulate delivery system having an enhanced flavor/sweetener capability.

In another embodiment, the flavor particles can be directly admixed with the molten hydrophobic/flavor enhancer mixture and then spread into sheets, allowed to cool and then ground into suitable particle sizes for use in comestible products. This method has disadvantages, however, since grinding tends to disrupt the continuity of the coating around the flavor particles and may result in a loss of enhancement provided by the intimate contact between the flavor enhancement component and the flavor particle itself. Thus, while it is useful in practicing the instant invention, it is preferred to use the spray congealing method described above.

As previously mentioned, the hydrophobic coating provides both a protective barrier to prevent interaction between the flavor particles and other components or chemicals present in a particular product, as well as providing a means to maintain a flavor/sweetener enhancer in intimate contact with the flavor particles. While it is not critical that the hydrophobic coating be a particular thickness, it should be present to effectively coat the flavor particles. If additional coating is required the delivery system particles can be left suspended in the air stream and additional spraying with the molten mixture can be performed.

As mentioned above, the delivery systems are useful in any number of comestible products. In particular, chewing gum, confectionary, pharmaceutical preparations, as well as other food products such as baked goods are among those comestible products which would benefit through enhanced flavor/sweetness provided by the inventive delivery system.

With regard to the chewing gum formulation in which the novel delivery system is employed, the amount of gum base employed will vary greatly depending on various factors such as the type of base used, consistency desired and other components used to make the final product. In general, amounts of about 5% to about 45% by weight of the final chewing gum composition are acceptable for use in chewing gum compositions with preferred amounts of about 15% to about 25% by weight. The gum base may be any water-insoluble gum base well known in the art. Illustrative examples of suitable polymers in gum bases include other natural and synthetic elastomers and rubbers. For example, those polymers which are suitable in gum bases, include, without limitation, substances of vegetable origin such as chicle, gelutong, gutta percha and crown gum. Synthetic elastomers such as butadiene-styrene copolymers, isobutylene-isoprene copolymers, polyethylene, polyisobutylene and polyvinylacetate and mixtures thereof, are particularly useful.

The gum base composition may contain elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythriol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin, such as polymers of alpha-pinene or beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like are useful, as well as natural waxes and petroleum waxes, such as polyurethane waxes, paraffin waxes and microcrystalline waxes. These ingredients may also be incorporated into the gum base to obtain a variety of desirable textures and consistency properties. These additional materials are generally employed alone or in combination in amounts of up to about 30% by weight and preferably in amounts of from about 3% to about 20% by weight of the final gum base composition.

The chewing gum composition may additionally include the conventional additives of flavoring agent, coloring agents such as titanium dioxide; emulsifiers such as lecithin and glyceryl monostearate; and additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum.

In the instance where auxiliary sweeteners are utilized in addition to those in the delivery system, the present invention contemplates the inclusion of those sweeteners well known in the art, including both natural and artificial sweeteners. Thus, additional sweeteners may be chosen from the following non-limiting list: sugars such as sucrose, glucose (corn syrup), dextrose, invert sugar, fructose, and mixtures thereof; chlorinated sucrose compounds such as sucralose and its derivatives; acid saccharin and its various salts such as the sodium saccharin or calcium saccharin; cyclamic acid and its various salts such as the sodium salt; the dipeptide sweeteners such as aspartame and various derivatives known to be sweet; dihydrochalcone compounds; glycyrrhizin; *Stevia rebaudiana* (Stevioside); and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Reissue Pat. No. 26,959. Also contemplated is the synthetic sweetener 3,6-dihydro-6-methyl-1-1,2,3-oxathiazin-4-one-2,2-dioxide particularly the potassium (Acesulfame-K), sodium and calcium salts thereof as described in Germany Patent No. 2,001,017.7.

Suitable flavorings include both natural and artificial flavors, and mints such as peppermint, menthol, artificial vanilla, cinnamon, various fruit flavors, both individual and mixed, and the like are contemplated. The flavorings are generally utilized in amounts that will vary depending upon the individual flavor, and may, for example, range in amounts of about 0.5% to about 3% by weight of the final chewing gum composition weight. The flavorings may be present in the delivery system, in the chewing gum composition itself, or both.

The colorants useful in the present invention, include the pigments such as titanium dioxide, and may be incorporated in amounts of up to about 1% by weight, and preferably up to about 0.6% by weight. Also, the colorants may include other dies suitable for food, drug and cosmetic applications, and known as F.D. & C. dyes and the like. The materials acceptable for the foregoing spectrum of use are preferably water-soluble. Illustrative examples include indigold die, known as F.D. & C. Blue No. 2, which is the disodium salt of 5,5'-indigotindisulfonic acid. Similarly, the dye known as F.D. & C. Green No. 1, comprises a triphenylmethane dye and is the monosodium salt of 4-[4-N-ethyl-p-sulfobenzylamino) diphenylmethylene]-[1-(N-ethyl-N-p-sulfoniumbenzyl)- $^{2,5}$-cyclohexadienimine]. A full recitation of all F.D. & C. and D. & C. and other corresponding chemical structures may be found in the Kirk-Othmer Encyclopedia of Chemical Technology, in Volume 5, at pages 857–884, which text is accordingly incorporated herein by reference.

The chewing gums of the invention may be in any form known in the art, such as stick gum, slab gum, chunk gum, shredded gum, hard coated gum, tabletted gum, as well as center-filled gum.

The process of preparing the inventive chewing gum compositions is as follows. The gum base is melted (about 85° to about 90° C.), cooled to 78° C. and placed in a pre-warmed (60° C.) standard mixing kettle equipped with sigma blades. The emulsifier (lecithin) is added and mixed. Next, a portion of the sugar alcohol (sorbitol) and the softener (glycerin) is added and mixed for an additional 3 to 6 minutes. The mixing kettle is cooled and the additional sweetener (mannitol) and the remainder of the sorbitol and glycerin are then added and mixing is continued. At this time, the unflavored chewing gum temperature is about 39°–42° C. Flavor oil is then added and incorporated into the base and the mixing is continued. Finally, the delivery system containing the core material is added and mixed for an additional 1 to 10 minutes. The delivery system is added as the last ingredient. The final gum temperature is about 39° C.–43° C. The chewing gum composition is then discharged from the kettle, rolled, scored and formed into chewing gum pieces.

The following examples serve to provide further appreciation of the invention but are not meant in any way to restrict the effective scope of the invention. All percentages throughout the specification are by weight % of the final delivery system unless otherwise indicated.

EXAMPLE I

Delivery systems of the instant invention were prepared in accordance with the following method. A mixture comprising 56.67% hard palm oil and 10% wax were melted in a kettle and blended to form a molten, homogeneous mixture. The melting point of the mixture was below about 100° to avoid any possibility of denaturing the flavor enhancer (e.g. thaumatin), which would result in loss of flavor and sweetness enhancing capability. The mixture was then combined with the about 5% by weight thaumatin and mixing was continued to obtain homogeneity, while still keeping the temperature below about 100° C. More specifically, the temperature was kept at about 85° to about 95° C. The encapsulation matrix was now ready to be fed into a spray congealing apparatus (Glatt GPC-15) fluidized bed granulator where it would be used to coat a fluidized bed of the powdered spray-dried flavor. The flavor particles were suspended in the granulator stream of cool air into which the encapsulation matrix was sprayed or atomized. Upon contact with the cooler air temperature and fluidized flavor particles, the molten encapsulating matrix solidified onto the flavor particles and passed out of the upward air stream. The nozzle pressure and temperature was regulated to control the final particle droplet size. The result was a dry particle or agglomerate, referred to herein as the delivery systm, having an approximate elliptical or spherical shape. The delivery system particles could then be sized for a particular application or allowed to remain in the granulator to obtain additional encapsulation coats.

EXAMPLE 2

The inventive delivery system was formed using the procedure of Example I whereby 10% of hard palm oil, 10% of paraffin wax, 30% of thaumatin and 50% of the spray dried flavor were used. The resultant product was dry, free-flowing and was capable of delivering a flavor/sweetness enhancement.

EXAMPLE 3

The procedure of Example 1 was repeated using 40% soybean oil, 25% microcrystalline wax, 10% thaumatin and 25% spray dried flavor.

EXAMPLE 4

The procedure of Example 1 was repeated using the same ingredients only monellin was used to replace the thaumatin.

EXAMPLE 5

The procedure of Example 1 was repeated using 70% rapeseed oil, 20% paraffin wax, 5% thaumatin and 5% spray dried flavor.

EXAMPLE 6

The procedure of Example 1 was repeated using 59.5% cottonseed oil, 5% carbo wax, 10% thaumatin and 20% spray dried flavor.

EXAMPLE 7

The procedure of Example 1 was repeated using the same ingredients except the solid high intensity sweetener aspartame was additionally incorporated with the powdered spray dried flavor, resulting in a delivery system encapsulating both flavor and sweetener.

EXAMPLE 8

The procedure of Example 1 was repeated using the same ingredients except the solid sweetener saccharin was additionally incorporated with the powdered spray dried flavor, resulting in a delivery system encapsulating both flavor and sweetener.

EXAMPLE 9

Sugar chewing gum compositions containing the novel delivery systems from previous examples were prepared in accordance with the formulations set forth below, employing conventional gum making techniques.

TABLE I

| Ingredient | Sugar Chewing Gum Compositions Containing Compositions - % Weight | | | | | | |
|---|---|---|---|---|---|---|---|
| | Control | P-1 | P-2 | P-3 | I-1 | I-2 | I-3 |
| Delivery System Example 1 | — | — | — | — | 0.005 | 0.015 | 0.03 |
| *Free thaumatin (in liquid flavor) | — | 0.005 | 0.015 | — | — | — | — |
| Free thaumatin (in spray dried flavor) | — | — | — | 0.015 | — | — | — |
| Gum base | 22.0 | 22.0 | 22.0 | 22.0 | 22.0 | 22.0 | 22.0 |
| Sugar | 66.4 | 66.395 | 66.3 | 66.37 | 66.3 | 66.4 | 66.37 |
| Filler | 4.0 | 4.0 | 4.0 | 4.0 | 4.0 | 4.0 | 4.0 |
| Softener | 5.5 | 5.5 | 5.5 | 5.5 | 5.5 | 5.5 | 5.5 |
| Color | 0.4 | 0.4 | 0.4 | 0.4 | 0.4 | 0.4 | 0.4 |
| Liquid flavor | 1.2 | 1.2 | 1.2 | 1.2 | 1.2 | 1.2 | 1.2 |
| Spray dried flavor | 0.5 | 0.5 | 0.59 | 0.53 | 0.5 | 0.5 | 0.53 |

*Thaumatin was first admixed with the flavor and then added to the chewing gum composition.

EXAMPLE 10

Sugarless chewing gum compositions containing the novel delivery system from previous examples were set forth below, employing conventional gum making techniques.

TABLE II

| Ingredient | Sugarless Chewing Gum Composition % Weight | | | |
|---|---|---|---|---|
| | P-4 | P-5 | I-4 | I-5 |
| Delivery System Example 1 | — | — | 0.015 | 0.015 |
| *Free Thaumatin (in liquid flavor) | — | 0.015 | — | — |
| Free Thaumatin (in spray dried flavor) | 0.0005 | — | — | — |
| Gum Base | 23 | 23 | 23 | 23 |
| Filler | — | — | 2.9 | 2.9 |
| Polyol | 62 | 52.4 | 58.5 | 58.4 |
| Aspartame | — | — | — | 0.2 |
| Saccharin | — | — | 0.14 | — |
| Softener | 12.5 | 12.5 | 13.5 | 13.5 |
| Color | 0.2 | 0.2 | 0.5 | 0.1 |
| Liquid Flavor | 1.2 | 1.2 | 1.5 | 1.5 |
| Spray Dried Flavor | 0.5 | — | — | — |

*Thaumatin was first admixed with the flavor and then added to the chewing gum composition.

SENSORY EVALUATION TESTS

An expert panel test was conducted on several chewing gum compositions having 0.015% thaumatin incorporated therein. The panelist were asked to rate flavor and sweetness enhancement on a hedonic scale of 0-100, where "0" represents very poor flavor and sweetness and 100 represent excellent (high) flavor and sweetness enhancement. Ratings for each composition were recorded at chew intervals of 0.5, 2, 6, 10 and 15 minutes. The results are depicted in the graph of FIG. I.

The graph in FIG. I shows panels evaluation results (blind studies) for four different chewing gum compositions. These compositions are taken from Table I. The control composition ("C") does not contain any form of a flavor enhancement and is representative of a commercially available, prior art chewing gum composition. Curve "D" on the graph represents P-3, which is a composition containing free thaumatin without the inventive delivery system encapsulation. Curve "F" represents P-2 wherein free thaumatin is admixed with liquid flavor and added directly to the gum composition. Curve "E" is representative of a chewing gum composition containing the inventive delivery system, namely I-2. It is clear from Table I that each of these compositions tested had formulations that except for the presence of delivery systems were otherwise substantially the same.

As clearly indicated by the curves, chewing gum compositions containing the inventive delivery system exhibited a significantly higher sweetener/flavor enhancement at all tested intervals of chew time. The most significant difference, however, is at the 15 minute chew interval, where gum compositions containing the delivery system were assigned a score of 30 as compared to scores of 0, 14, and 20. At all times through the chew intervals, the inventive composition gave higher perceived sweetener and flavor enhancement than any of the prior art compositions.

The invention being thus described, it will be obvious that the same may be varied in many ways. Such variations are not to be regarded as a departure from the spirit and scope of the invention and all such modifications are intended to be included within the scope of the following claims.

We claim:

1. A free flowing particulate delivery system for providing enhanced flavor and sweetness to comestible compositions, said delivery system comprising:
   (A) a powdered flavor composition; and
   (B) an encapsulating matrix for said powdered flavor composition;
   wherein said matrix comprises flavor/sweetness enhancers present in amounts of about 1 to about 30% by weight of said delivery system selected from the group consisting of thaumetin, monellin, dihydrochalcones and mixtures thereof and a hydrophobic material present in amounts of about 10% to about 70% by weight of said delivery system selected from the group consisting of waxes, fats and mixtures thereof.

2. The delivery system of claim 1 wherein the powdered flavor composition is a spray dried natural or artificial flavor or essence.

3. The delivery system of claim 2 wherein the spray dried flavor is selected from the group consisting of spearmint flavor, peppermint flavor, cinnamon flavor, fruit flavors, fruit essences, kola flavor, kola extract and mixtures thereof.

4. The delivery system of claim 1 wherein the flavor composition is present in amounts of about 5 to about 50% by weight.

5. The delivery system of claim 1 wherein the flavor composition is present in amounts of about 20 to about 30% by weight.

6. The delivery system of claim 1 wherein the flavor/sweetness enhancer is present in amounts of about 5 to about 20% by weight of said delivery system; and the hydrophobic material is present in amounts of about 40 to about 58% by weight of said delivery system; and the hydrophobic material is present in amounts of about 40 to about 58% by weight of said delivery system.

7. The delivery system of claim 1 wherein the flavor enhancer is present in amounts sufficient to produce sweetness as well as flavor enhancement.

8. The delivery system of claim 1 wherein the hydrophobic fat material is a fatty acid selected from the group consisting of hydrogenated or partially hydrogenated oils.

9. The delivery system of claim 8 wherein the hydrogenated or partially hydrogenated oils are selected from the group consisting of palm oil, palm kernel oil, peanut oil, rapeseed oil, rice bran oil, soybean oil, cottonseed oil, sunflower oil, safflower oil and mixtures thereof.

10. The delivery system of claim 1 wherein the hydrophobic fat material is selected from the group consisting of monoglycerides, diglycerides, triglycerides, polyglycerol esters, sorbitol esters and mixtures thereof.

11. The delivery system of claim 1 wherein the hydrophobic fat material is present in amounts of about 45 to about 55% by weight.

12. The delivery system of claim 1 wherein the hydrophobic wax material is selected from the group consisting of natural waxes, synthetic waxes and mixtures thereof.

13. The delivery system of claim 1 wherein the hydrophobic wax material is selected from the group consisting of paraffin wax, beeswax, carnuba wax, candelilla wax, lanolin, bayberry wax, sugar cane, petrolatum, carbowax, spermaceti wax, rice bran wax, microcrystalline wax and mixtures thereof.

14. A process of preparing a flavor delivery system capable of providing flavor encapsulation as well as enhanced flavor and sweetness comprising the steps of:
   (A) providing a molten homogeneous mixture of fat, wax or mixtures thereof in amounts of about 10% to about 70% by weight of said delivery system and maintaining this mixture at a temperature below the denaturation temperature of thaumatin, monellin, or dihydrochalcones;
   (B) adding thaumatin, monellin, dihydrochalcones or mixtures thereof in amounts of about 1 to about 30% by weight of said delivery system to the molten mixture at a temperature of about 70° to about 90° C. and mixing to obtain homogenity;
   (C) providing a fluidizing air stream of a powdered flavor composition having a temperature below the melting point of the molten mixture of (B);
   (D) spraying the molten mixture of (B) onto the fluidized stream of powdered flavor composition to form a congealed encapsulation coating on said powdered flavor composition.

15. The process of claim 14 wherein the molten mixture is formed at a temperature sufficient to remain molten but below about 100° C.

16. The process of claim 14 wherein the molten encapsulation is formed at a temperature sufficient to remain molten but below about 80° C.

17. The process of claim 14 wherein the spray rate of the molten mixture is kept at about 15 to about 20 ml/minute and the temperature of the fluidized air stream of powdered spray dried flavor is about 70° to about 75° C.

18. The process of claim 14 wherein the homogenous molten mixture provided in step (A) comprises a material selected from the group consisting of natural or synthetic waxes, hydrogenated or partially hydrogenated fatty acids, monoglycerides, diglycerides, triglycerides, sorbitol esters, polyglycerol esters and mixtures thereof.

19. The delivery system of claim 1 incorporated into a chewing gum composition.

20. The delivery system of claim 1 incorporated into a confectionery composition.

21. The delivery system of claim 1 incorporated into a pharmaceutical composition.

22. The delivery system of claim 1 incorporated into a food product.

23. The delivery system of claim 1 incorporated into a dentifrice composition or denture adhesive.

* * * * *